(12) United States Patent
Shim

(10) Patent No.: US 6,361,511 B1
(45) Date of Patent: Mar. 26, 2002

(54) ADJUSTABLE MASSAGING EXERCISER WORN ON WRIST

(76) Inventor: Henry H. Shim, 1124 S. Kingsley Dr., Los Angeles, CA (US) 90006

( * ) Notice: Subject to any disclaimer, the term of this patent is extended or adjusted under 35 U.S.C. 154(b) by 0 days.

(21) Appl. No.: 09/561,889

(22) Filed: May 1, 2000

(51) Int. Cl.⁷ .................................................. A61H 7/00
(52) U.S. Cl. ........................ 601/137; 601/135; 601/33; 482/44; 482/48
(58) Field of Search ................................ 601/134, 135, 601/136, 137, 138, 143, 23, 33, 40; 402/44, 45, 47, 48

(56) References Cited

U.S. PATENT DOCUMENTS

| 720,847 | A | * | 2/1903 | Sanford | |
|---|---|---|---|---|---|
| 904,800 | A | * | 11/1908 | Nelson | |
| 1,208,064 | A | * | 12/1916 | Wilber | |
| 2,533,036 | A | * | 12/1950 | Moscowitz | 128/62 |
| 3,711,889 | A | * | 1/1973 | Jennings | 15/227 |
| 4,249,521 | A | * | 2/1981 | Gueret | 128/62 R |
| 5,577,997 | A | * | 11/1996 | Thariani et al. | 601/135 |

* cited by examiner

Primary Examiner—Michael A. Brown
Assistant Examiner—Benjamin K. Koo
(74) Attorney, Agent, or Firm—John K. Park; Park & Sutton LLP

(57) ABSTRACT

An adjustable massaging exerciser worn on a wrist comprises a flexible band member and a string. The flexible band member has a first end, a second end, an upper end, a lower end, an outer peripheral surface, and a pair of elongated holes. The first end and the second end circularly approach each other with a hiatus therebetween so that each of the upper end and the lower end forms an open loop. The holes are respectively formed through the upper and lower ends and in an opposite adjacency to the hiatus. A plurality of bosses are formed on the outer peripheral surface. The string has string ends and is flexibly placed through the first hole and the second hole while forming a flexible hook about the lower end of the band member. The string ends are hooked at upper entrances of the holes to support the flexible hook that can be hooked on a user's finger or a thumb.

20 Claims, 3 Drawing Sheets

ADJUSTABLE MASSAGING EXERCISER WORN ON WRIST

BACKGROUND OF THE INVENTION

The present invention relates to a massager. More particularly, the present invention relates to an adjustable massaging exerciser worn on a wrist which facilitates a body massage while taking a bath or a shower.

Taking a shower or a bath is known as one of the best ways to release stress and revitalize metabolism. Statistics show that an individual in the current society wants to most increase time for shower along with time for jogging. When taking a shower, palms and fingers are most used to rub and massage the body. The massaging and rubbing effect on the body can be most realized with the help of a rubbing towel.

However, when using such a rubbing towel or a pad, one has to suffer nuisances to reach out and put it back where it is since the rubbing towel is nothing but to cause a shower taker to get less exposed to the shower. The more exposed to the shower, the more relaxed.

Accordingly, there is a need for using a rubbing material without interruption while taking a shower.

SUMMARY OF THE INVENTION

The present invention is contrived to overcoming the conventional disadvantages. Therefore, it is an object of the present invention to provide an adjustably massaging exerciser worn on a wrist which enables a user to realize a thorough relaxation without interruption while enjoying a massaging effect at a shower.

Another object of the present invention is to improve an exercising effect by causing the exerciser-worn arm to frequently move around the body.

To achieve the above-described objects, an adjustable massaging exerciser according to the present invention comprises a flexible band member, a plurality of bosses, and a string. The flexible band member has a first end, a second end, an upper end, a lower end, an outer peripheral surface, and a pair of elongated holes. The first end and the second end circularly approach each other with a hiatus therebetween so that each of the upper end and the lower end forms an open loop. The elongated holes are respectively formed through the upper end and the lower end and in an opposite adjacency to the hiatus.

The plurality of bosses are formed on the outer peripheral surface. The string has string ends and it is flexibly placed through the first hole and the second hole while forming a flexible hook about the lower end of the band member. The string ends are hooked at upper entrances of the elongated holes to support the flexible hook so that the flexible hook can be hooked on a user's finger or a thumb when the massaging exerciser is worn on the user's wrist.

In a preferred version, for a detachable attachment between the first end and the second end when the string is hooked on the user's finger or thumb, an attaching means may be formed on the first and second ends. The attaching means can be one selected from a hook and pile, a magnet, a rubber string, and other known attaching materials.

The outer peripheral may be made of rubber. The bosses may be made of rubber. Also, the flexible band member may be made of rubber. For a better performance, the flexible band member is at least 0.3 inches thick.

In an embodiment, a magnet may be embedded in at least one of the plurality of bosses. The flexible band member may further comprise a middle layer embedded therein and substantially exposed to the upper end thereof between the elongated holes, wherein the middle layer is made of sponge.

In another embodiment, the string may flexibly loop through the first hole and the second hole while forming a flexible hook about the lower end of the band member so that the flexible hook can be hooked on a user's finger or a thumb when the massaging exerciser is worn on the user's wrist. Also, a fastener may be provided to controllably tighten the string adjacent to the upper end of the flexible band member. Preferably, the fastener may be formed in a spherical shape with a through hole for controllably allowing the string therethrough.

An advantage of the present invention is to provide a massaging tool which enables a user to enjoy a further relaxation together with a shower or a bath. Another advantage is to maximize a massaging effect by providing the plurality of bosses on the outer peripheral surface of the flexible band member.

Most of all, the string-applied massaging exerciser can be adjustably worn on the wrist and stably maintained while taking a shower or a bath, thereby increasing usability. In addition, a sponge as the middle layer is exposedly placed within the band member so that the massaging exerciser can remain watery irrespective of shower exposure, thereby smoothing the skin contact of the bosses.

BRIEF DESCRIPTION OF THE DRAWINGS

The present invention will be better understood with reference to the accompanying drawings, wherein.

DETAILED DESCRIPTION OF THE PREFERRED EMBODIMENTS

Figure 1:
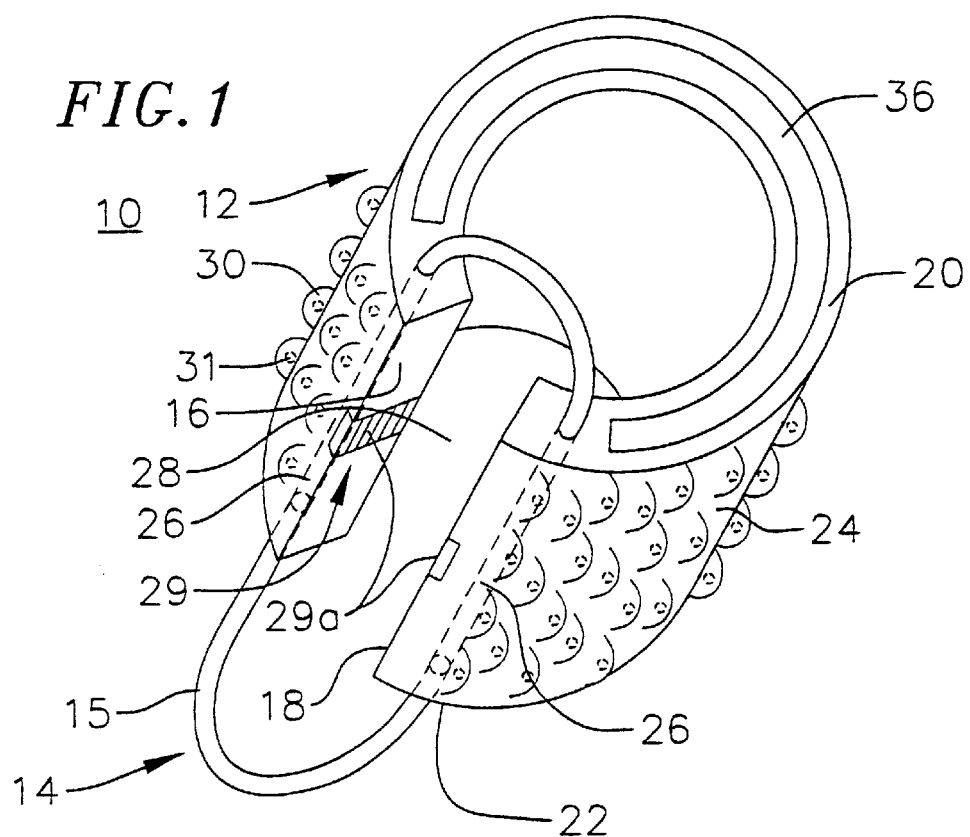
FIG. 1 is a perspective view showing an open state of an adjustable massaging exerciser according to an embodiment of the present invention.

As shown in FIG. 1, an adjustable massaging exerciser 10 that can be worn on a wrist according to the present invention comprises a flexible band member 12 and a string 14. When spread out without the string 14, the flexible band member 12 may be rectangular in shape. A preferred material for the flexible band member 12 is rubber. Other flexible materials such as sponge can be also used for the band member 12.

The flexible band member 12 has a first end 16 and a second end 18 at the approach to each other. The circled flexible band member 12 also has an upper end 20, a lower end 22, and an outer peripheral surface 24. The length between the upper end 20 and the lower end 22 may vary between about 1.5 inches and 5 inches. A pair of elongated holes 26 are formed through the flexible band member 12 from the upper end 20 to the lower end 22 and adjacent to the first and second ends 16, 18.

The first end 16 and the second end 18 circularly approach each other with a hiatus 28 therebetween so that each of the upper end 20 and the lower end 22 may form an open loop. Specifically, the elongated holes 26 are respectively formed through the upper end 20 and the lower end 22 and in an opposite adjacency to the hiatus 28. In this construction, the string 14 serves to maintain the first end 16 and the second end 18 together. In order to provide a detachable attachment between the first end 16 and the second end 18 when the string 14 is hooked on the user's finger or thumb, an attaching means 29 may be formed on the first and second ends 16, 18. The attaching means 29 can be one selected from a hook and pile 29a, a magnet, a rubber string, and other known attaching materials.

In a preferred version, a plurality of bosses 30 are formed on and along the outer peripheral surface 24. The plurality of bosses 30 serve to massage a user's body when gently rubbed on. The bosses 30 may be shaped in hemisphere, cone, cylinder, semi-oval, cube or other polyhedrons. In case of the hemispheric shape, the size of each boss 30 may vary between about 0.1 inch and about 1.0 inch in diameter. The preferred size of each boss 30 is 0.3 inches in diameter. The bosses 30 may be formed of rubber or other flexible materials. As further shown in FIG. 2, at least one of the plurality of bosses 30 has a magnet 31 embedded therein. As is well known, the magnet 31 serves to urge the blood circulation when contacted to a body portion, thereby improving a massage effect.

Figure 2:
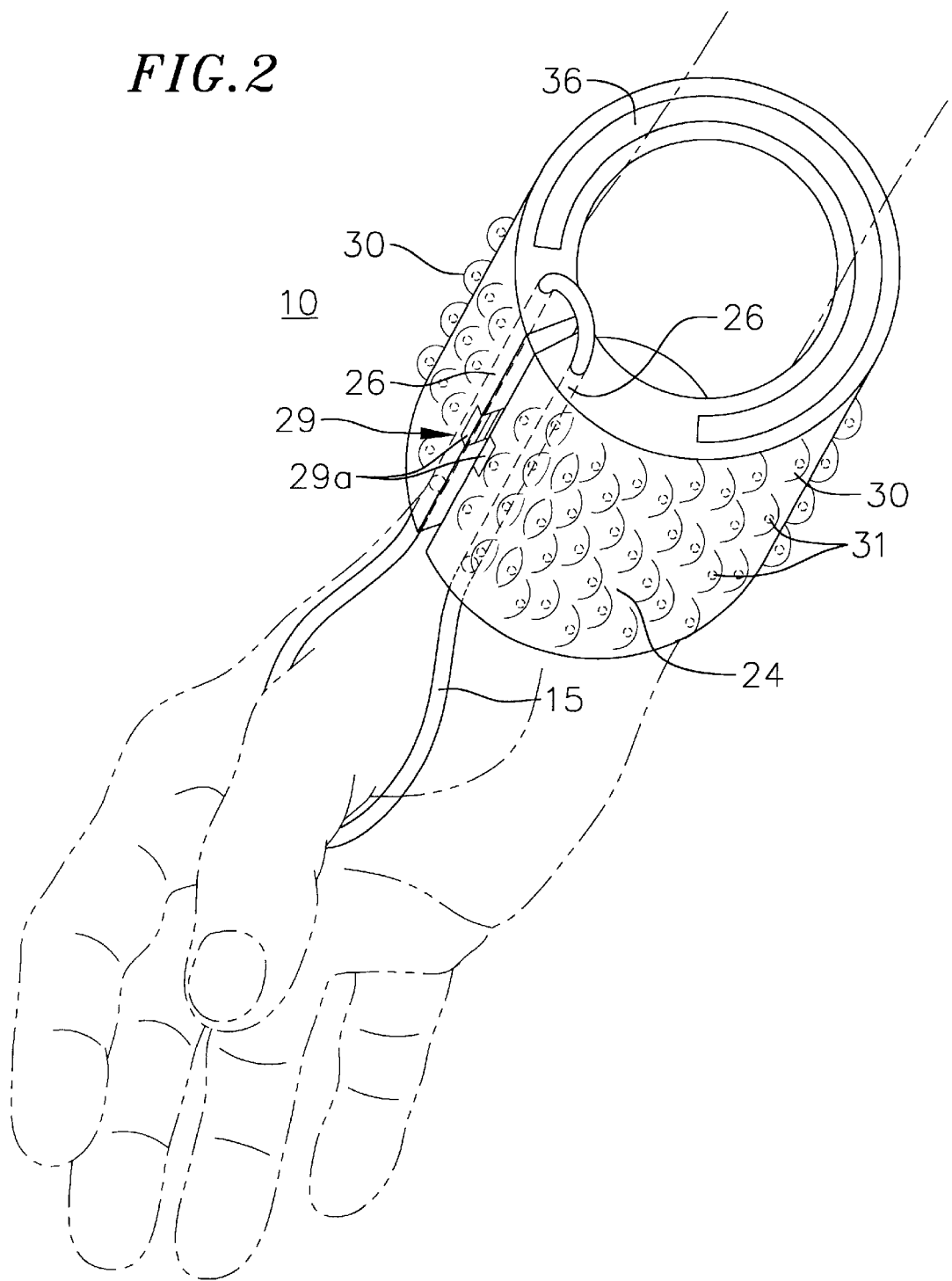
FIG. 2 is a perspective view showing a closed state of the adjustable massaging exerciser in FIG. 1 when worn on a wrist.
Figure 4:
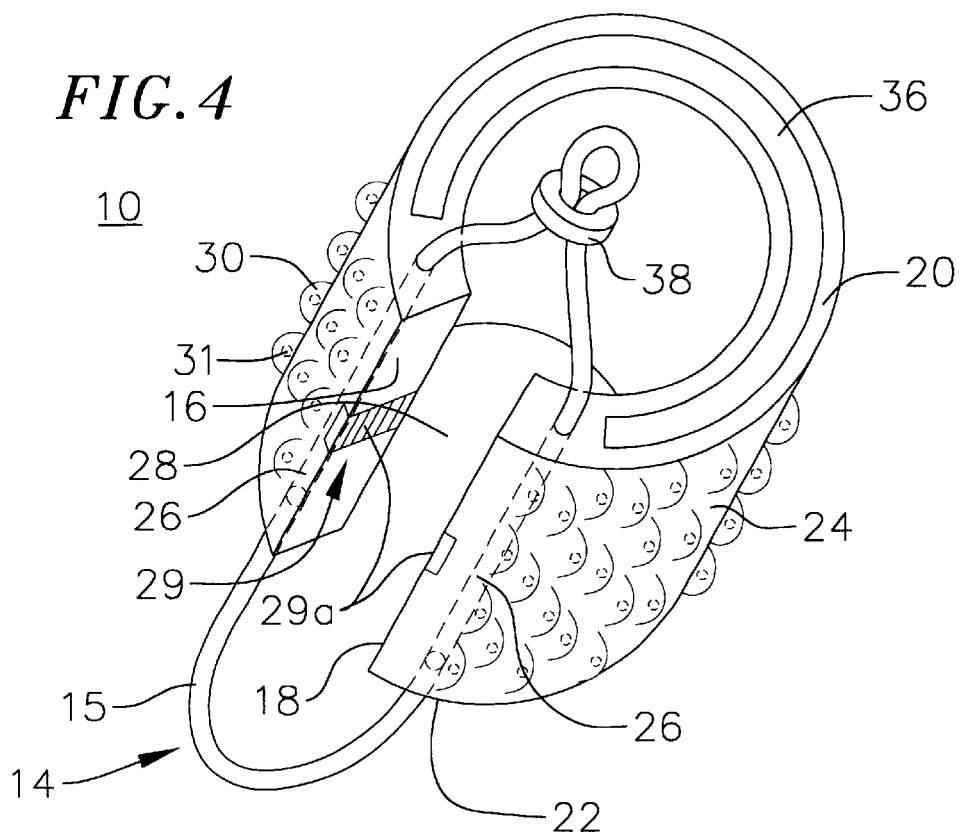
FIG. 4 is a perspective view showing the string tightened by a fastener of FIG. 1.
Figure 5:
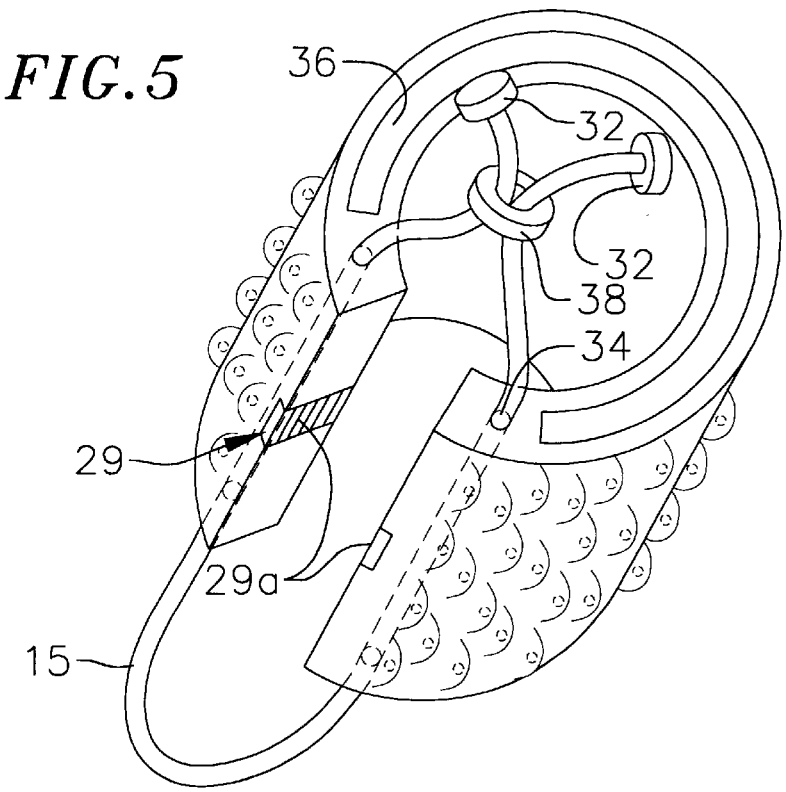
FIG. 5 is a perspective view showing the string tightened by the faster of FIG. 3.

According to an embodiment, the string 14 flexibly loops through the pair of through holes 26 while forming a flexible hook about the lower end 22 of the flexible band member 12. The flexible hook can be hooked on a user's finger or a thumb when the massaging exerciser 10 is worn on the user's wrist as shown in FIG. 2. The string 14 may be formed of rubber or fabric material.

Figure 3:
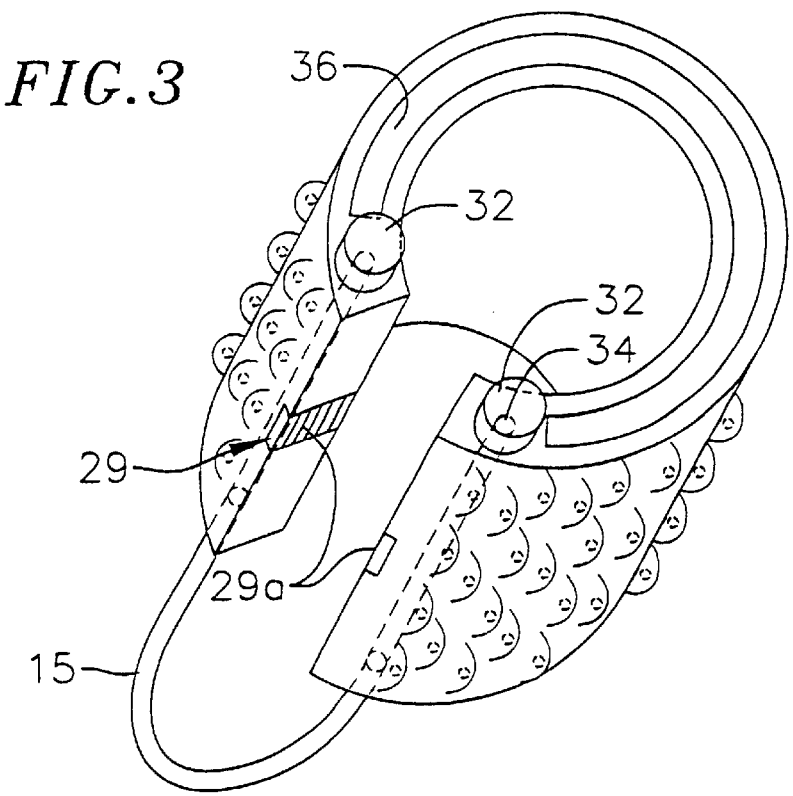
FIG. 3 is a perspective view showing an open state of an adjustable massaging exerciser according to another embodiment of the present invention.

As shown in FIG. 3, in another embodiment, the string 14 has string ends 32. The string 14 is flexibly placed through the pair of elongated holes 26 while also forming a flexible hook about the lower end 22 of the band member 12. In this structure, the string ends 32 are hooked at upper entrances 34 of the elongated holes 26 to support the flexible hook formed by the string 14 near the lower end 22.

For a better performance, the flexible band member 12 may have a middle layer 36 embedded therein and substantially exposed to the upper end 20 thereof between the elongated holes 26. The middle layer 36 can also be exposedly formed on the lower end 22. Preferably, the middle layer 36 is made of sponge. The middle layer 36 serves to absorb water so that the outer peripheral surface 24 with the bosses 30 can remain watery even when placed out of the shower or the bath water, thereby smoothing the skin contact of the bosses 30.

Likewise, the adjustable massaging exerciser 10 is worn on a wrist when taking a shower or a bath. Using the flexibility of the band member 12 and the string 14, the massaging exerciser 10 can be flexibly and easily worn on the user's wrist. With the band member 12 on the wrist, a string portion 15 near the lower end 22 becomes hooked on a thumb or a finger. At this time, the string 14 is naturally pulled down by the hookup and accordingly the hiatus 28 between the first end 16 and the second end 18 becomes smoothly narrowed to appropriately tighten the user's wrist.

In order to further control the string 14, a fastener 38 may be provided to controllably tighten the string 14 adjacent to the upper end 20 of the flexible band member 12 so that the massaging exerciser 10 can be adjustably worn on a user's wrist regardless of the size of the user's hand or wrist. Preferably, the fastener 38 may be formed in a spherical shape with a through hole for controllably allowing the string 14 therethrough.

An advantage of the present invention is to provide a massaging tool which enables a user to enjoy a further relaxation together with a shower or a bath. Another advantage is to maximize a massaging effect by providing the plurality of bosses on the outer peripheral surface of the flexible band member.

Most of all, the string-applied massaging exerciser 10 can be adjustably worn on the wrist and stably maintained while taking a shower or a bath, thereby increasing usability. In addition, a sponge as the middle layer 36 is exposedly placed within the band member 12 so that the massaging exerciser 10 can remain watery irrespective of shower exposure, thereby smoothing the skin contact of the bosses 30.

Although the invention has been described in considerable detail with reference to certain preferred versions thereof, other versions are possible by converting the aforementioned construction. For example, a sound device such as a bell can be attached to the string 14 so that the user can be amused while using the massaging exerciser 10 at the shower or at the bath. Therefore, the scope of the invention shall not be limited by the specification specified above and the appended claims.

What is claimed is:

1. An adjustable massaging exerciser worn on a wrist comprising:
   a) a flexible band member having a first end, a second end, an upper end, a lower end, an outer peripheral surface, and a pair of elongated holes, wherein the first end and the second end circularly approach each other with a hiatus therebetween so that each of the upper end and the lower end forms an open loop, and wherein the elongated holes are respectively formed through the upper end and the lower end and in an opposite adjacency to the hiatus;
   b) a plurality of bosses formed on the outer peripheral surface; and
   c) a string having string ends and flexibly placed through the first hole and the second hole while forming a flexible hook about the lower end of the band member, wherein the string ends are hooked at upper entrances of the elongated holes to support the flexible hook, wherein the flexible hook can be hooked on a user's finger or a thumb when the massaging exerciser is worn on the user's wrist.

2. The massaging exerciser of claim 1, wherein the flexible band member further comprises a middle layer embedded therein and substantially exposed to the upper end thereof between the elongated holes, wherein the middle layer is made of sponge.

3. The massaging exerciser of claim 2 further comprising an attaching means for detachably attaching the first end and the second end when the string is hooked on the user's finger or thumb.

4. The massaging exerciser of claim 3, wherein the outer peripheral surface is made of rubber.

5. The massaging exerciser of claim 4, wherein the bosses are made of rubber.

6. The massaging exerciser of claim 5, wherein the flexible band member is made of rubber.

7. The massaging exerciser of claim 6, wherein the flexible band member is at least 0.3 inches thick.

8. The massaging exerciser of claim 7 further comprising a magnet embedded in at least one of the plurality of bosses.

9. The massaging exerciser of claim 8 further comprising a fastener for controllably tightening the string adjacent to the upper end of the flexible band member.

10. The massaging exerciser of claim 9, wherein the fastener is formed in a spherical shape with a through hole for controllably allowing the string therethrough.

11. An adjustable massaging exerciser worn on a wrist comprising:
   a) a flexible band member having a first end, a second end, an upper end, a lower end, an outer peripheral surface, and a pair of elongated holes, wherein the first end and the second end circularly approach each other with a hiatus therebetween so that each of the upper end and the lower end forms an open loop, and wherein the elongated holes are respectively formed through the upper end and the lower end and in an opposite adjacency to the hiatus;
   b) a plurality of bosses formed on the outer peripheral surface; and
   c) a string flexibly looping through the first hole and the second hole while forming a flexible hook about the lower end of the band member, wherein the flexible hook can be hooked on a user's finger or a thumb when the massaging exerciser is worn on the user's wrist.

12. The massaging exerciser of claim 11, wherein the flexible band member further comprises a middle layer embedded therein and substantially exposed to the upper end thereof between the elongated holes, wherein the middle layer is made of sponge.

13. The massaging exerciser of claim 12 further comprising an attaching means for detachably attaching the first end and the second end when the string is hooked on the user's finger or thumb.

14. The massaging exerciser of claim 13, wherein the outer peripheral surface is made of rubber.

15. The massaging exerciser of claim 14, wherein the bosses are made of rubber.

16. The massaging exerciser of claim 15, wherein the flexible band member is made of rubber.

17. The massaging exerciser of claim 16, wherein the flexible band member is at least 0.3 inches thick.

18. The massaging exerciser of claim 17 further comprising a magnet embedded in at least one of the plurality of bosses.

19. The massaging exerciser of claim 18 further comprising a fastener for controllably tightening the string adjacent to the upper end of the flexible band member.

20. The massaging exerciser of claim 19, wherein the fastener is formed in a spherical shape with a through hole for controllably allowing the string therethrough.

* * * * *